United States Patent [19]

Labouze et al.

[11] Patent Number: 4,978,339
[45] Date of Patent: Dec. 18, 1990

[54] NON-REUSABLE SYRINGE

[76] Inventors: Joseph Labouze, 53, Bld. d'Andilly, Soisy/Montmorency, France, 95230; Pierre Teboul, 4, Av. Aristide Briand, Domont, France, 95330

[21] Appl. No.: 388,166

[22] Filed: Aug. 1, 1989

[30] Foreign Application Priority Data

Aug. 1, 1988 [FR] France ............... 88 10368

[51] Int. Cl.5 ............................. A61M 5/00
[52] U.S. Cl. .................. 604/110; 604/210; 604/218
[58] Field of Search .......... 604/110, 218, 220, 228, 604/210, 208

[56] References Cited

U.S. PATENT DOCUMENTS

| 3,890,971 | 6/1975 | Leeson et al. | 604/220 |
|---|---|---|---|
| 4,246,898 | 1/1981 | Travalent et al. | 604/220 |
| 4,642,102 | 2/1987 | Ohmori | 604/220 |
| 4,790,822 | 12/1988 | Haining | 604/110 |
| 4,820,272 | 4/1989 | Palmer | 604/220 |
| 4,826,483 | 5/1989 | Molnar | 604/110 |
| 4,840,616 | 6/1989 | Banks | 604/110 |

FOREIGN PATENT DOCUMENTS

| 0272035 | 6/1988 | European Pat. Off. | |
| 2593069 | 7/1987 | France . | |
| 2015883 | 9/1979 | United Kingdom . | |
| 8900432 | 1/1989 | World Int. Prop. O. | 604/110 |
| 8904185 | 5/1989 | World Int. Prop. O. | 604/110 |

Primary Examiner—C. Fred Rosenbaum
Assistant Examiner—Sharon Rose
Attorney, Agent, or Firm—Darby & Darby

[57] ABSTRACT

The piston stem (6) of the non-reusable syringe carries radial ribs (7, 9) having a saw-tooth profile (20, 21) cooperating with a stop (19) fixed to the inner wall of the syringe body, for allowing the piston (1) to be moved in one direction only, so that the syringe can be used only once.

9 Claims, 1 Drawing Sheet

NON-REUSABLE SYRINGE

BACKGROUND OF THE INVENTION

This invention relates to a non-reusable syringe.

The utilization of disposable syringes has now become generalized. Such syringes are used only once and are then discarded. It occurs, however, particularly among drug addicts, that one same syringe will be used by several persons thus causing the transmission of diseases, particularly of AIDS.

One purpose of this invention is to provide a syringe which cannot be used again after having been used once.

BRIEF DESCRIPTION AND OBJECTS OF THE INVENTION

The invention has for its object a non-reusable syringe, of the type comprising a syringe body and a piston having a longitudinal stem carrying ribs which extend radially along said stem, perpendicular to each other.

According to the invention, this syringe is characterized in that at least two of the ribs present an edge with a saw-tooth profile cooperating with a stop for allowing the piston to be moved in one direction only for each rib having a serrated edge.

According to further features of this invention a stop is disposed in a slot of an annular member which partly closes up the syringe body.

The annular member presents a central circular aperture provided with two angularly spaced slots, the stop being arranged within one of said slots.

Those ribs having a saw-tooth profile have a longer radial extension than the other ribs and extend into the slots of the annular member.

Also, the other ribs do not have a saw-tooth profile and have a shorter radial extension, so that they may pass freely through the central aperture of the annular member.

On one end of their edge having a saw-tooth profile, the ribs present a notch which allows the piston to be rotated about its axis when said notch is in registry with the annular member, in such manner that, when the piston has been retracted for filling the syringe, it can be rotated by a half-turn until the second serrated rib takes the place of the first serrated rib, thus allowing the piston to be pushed lengthwise for making an injection.

The syringe body is formed of a cylindrical barrel and of an end cap welded together in fluid-tight manner.

BRIEF DESCRIPTION OF THE DRAWINGS

Further features of this invention will be apparent from the following detailed description and from the appended drawing which represents.

DETAILED DESCRIPTION OF THE INVENTION

Figure 1:
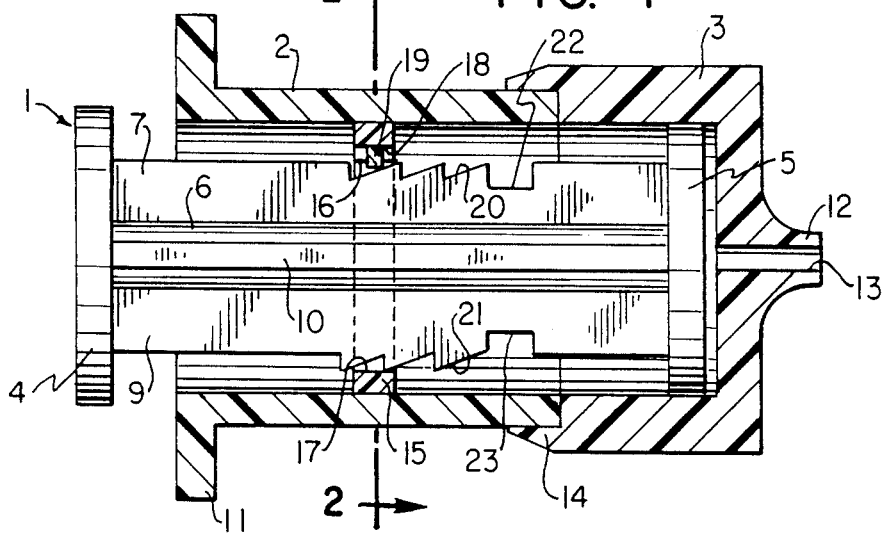
FIG. 1 is a syringe according to this invention, partly cut-out along its longitudinal axis.

Referring to FIG. 1, it will be seen that the syringe according to the invention is essentially composed of a piston 1 and of a body formed of two assembled parts, namely a cylindrical barrel 2 and an end cap 3.

Piston 1 carries on its external end, outside the barrel 2, a circular handgrip 4, and on its inner end, inside the barrel 2, a disk-shaped piston head 5 slidably engaged with the inner wall of the barrel 2. The handgrip 4 and the piston head 5 are joined together by a piston stem 6 carrying ribs 7, 8, 9 and 10 which extend radially about the piston stem 6. Ribs 8 and 10 are diametrically opposed to each other and have a shorter radial extension than the serrated ribs 7 and 9, while they extend perpendicularly to these serrated ribs 7 and 9. One function of these shorter ribs 8 and 10 is to act as stiffening members for the piston assembly comprising the handgrip 4, the piston head 5 and the piston stem 6.

The two ribs 7 and 9, which have a greater radial extension present, on a longitudinal portion of their outer free edge, a saw-tooth profile, the function of which will be explained hereinafter.

The syringe body comprises a cylindrical barrel 2 carrying on one of its ends a retaining ring 11 of conventional type, and on the other end a terminal cap 3 comprising a hollow cylindrical portion which fits tightly over the end of the barrel 2 and an end flange provided with a nozzle 12 for receiving an injection needle (not shown). A passage 13 is provided in the nozzle 12 for the fluid to be injected. Alternatively, the cap 3 bears an incorporated injection needle. The cap 3 is provided with a ring 14 surrounding the end of the barrel 2, this ring being designed for receiving an annular welded seam for ensuring a fluid-tight sealed assembly of barrel 2 with cap 3.

Figure 2:
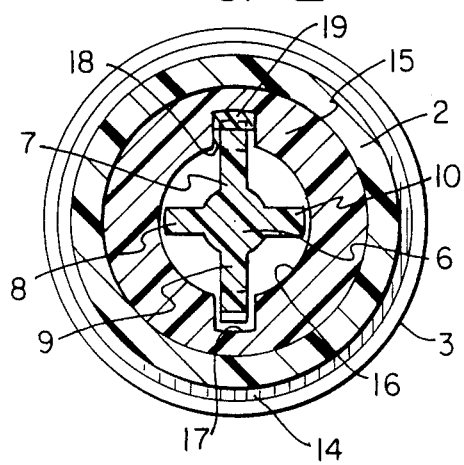
FIG. 2 is a cross-sectional view of the syringe, taken along line II—II of FIG. 1.

Inside the barrel 2 is disposed an annular member 15 which is represented in more detail in FIG. 2. This annular member 15 is fixed inside the barrel 2, for instance by gluing. Its outer diameter matches the internal diameter of barrel 2. The annular member 15 presents a central circular aperture 16, two diametrically opposed slots 17 and 18 being formed in the internal edge of the annular member 15. In one of these slots, say slot 18 for instance, a stop 19 is disposed for cooperating with the saw-tooth edges of ribs 7 and 9.

The circular aperture 16 of the annular member 15 has a diameter sufficient for allowing ribs 8 and 10, which have a shorter radial extension, to pass freely therethrough, without friction. On the other hand, ribs 7 and 9 having a greater radial extension can only be inserted into the diametrically opposed slots 17 and 18. With this arrangement, the piston is oriented and guided in its longitudinal displacement, and the stop 19 is thus enabled to cooperate with the saw-tooth profile of the serrated ribs 7 and 9.

The serrated rib 7 presents a saw-tooth profile 20 in which the steep flanks of the teeth are oriented so that the piston 1 will be allowed to be retracted for filling the syringe, but that they will not allow the piston to be pushed forward for carrying out an injection. On the other hand, the other serrated rib 9 presents a similar saw-tooth profile 21 which will allow the piston to be pushed forward for carrying out an injection, but will not allow the piston to be retracted for filling the syringe again.

On one end of the saw-tooth edge of each serrated rib 7 and 9, in the vicinity of the piston head 5, there is provided a notch, respectively notch 22 on rib 7 and notch 23 on rib 9. When the piston 1 is retracted so that notch 22 comes into registry with the annular member, this will allow piston 1 to be rotated about its longitudinal axis. This possibility of rotating the piston is used in the following manner:

Piston 1 being in place in the syringe barrel 2, rib 7 being lodged in the slot 18 of the annular member 15, and the saw-tooth edge 20 resting against the stop 19, the piston 1 can be retracted for filling the syringe. The flanks of the teeth of the saw-tooth edge 20 having a gentle slope are allowed to pass beyond the stop 19, as they deform plastically, while the steep flanks of the teeth will abut against the stop 19, preventing the piston 1 being pushed forward for an injection. When the notch 22 comes into registry with the annular member 15, the piston may then be rotated about its axis by one half-turn, until the serrated rib 7 becomes lodged inside slot 17 and the other serrated rib 9 becomes lodged inside the opposite slot 18.

The piston 1 may then be pushed forward for carrying out an injection. The gently sloping flanks of the teeth of the saw-tooth profile are able to pass, one after the other, beyond the stop 19, as they deform plastically, while the steep flanks of the teeth will abut firmly against the stop 19, thus prohibiting the piston 1 to be retracted. When the injection is completed, the piston 1 is blocked in its final position. It cannot be retracted, because the steep flanks of the serrated edge 21 abutting against the stop 19 prevent any rearward motion. Also, the piston 1 cannot be rotated about its axis, since the ribs 7 and 9 are engaged respectively in the slots 17, 18 of the annular member 15 and are firmly held in these slots. The syringe will therefore be non-reusable.

The syringe according to this invention cannot be assembled in the same manner as a conventional syringe. This is why it is made of several parts which need to be assembled sequentially in a precise order.

At first, the annular member 15 is inserted into the barrel 2, and located in the proper position. It will then be fixed, for instance by gluing.

The piston 1 is then inserted into the barrel 2. In this operation, the piston is not yet provided with one of its end pieces, either the piston head 5 or the handgrip 4. If the piston head 5 has not yet been assembled with the piston stem 6, then the piston will be inserted into the barrel end carrying the retaining ring 11. On the other hand, if the handgrip 4 has not yet been assembled with the stem 6, then the piston will be inserted into the other end of the barrel 2, namely the barrel end onto which the end cap 3 will subsequently be fitted.

The missing end piece, 4 or 5, of the piston is then assembled with the stem 6, for instance by ultrasonic welding.

The next operation will consist in fitting the end cap 3 over the barrel 2, with the ring 14 of the cap 3 surrounding the end of the barrel. Again, the assembly of cap 3 with the barrel 2 can be secured by ultrasonic welding. This assembly of cap 3 with barrel 2 will obviously need to be fluid-tight. The syringe will then be ready for being used only once, and it will not be reusable.

To enhance the non-reusable character of the syringe, piston 1 can be made breakable in a plane perpendicular to its axis and situated between the handgrip 4 and the saw-tooth profile 21. To this end may be provided in the ribs 7-10 lines of attenuated strength, for example score lines which reduce the material thickness, and in the stem 6 a weakness point. Thus, after using the syringe, if one tries to reuse it by a strong pulling on piston 1, such piston breaks and thus confirms the impossibility to reuse the syringe.

What is claimed is:

1. A non-reusable syringe comprising:
   a hollow syringe body having a first end to which the cannula is to be attached and a second end,
   a piston for insertion into the body second end and for travel within said body, the piston having a longitudinally extending stem with a pair of spaced apart radially extending ribs, each of said ribs having on its outer edge a ratchet tooth profile, the profile of the teeth on each rib extending in the opposite direction,
   means within the body forming a pair of slots at a position corresponding to the pair of spaced ribs of the stem, one of said slots having a stop means for engaging the teeth of a rib profile and the other slot permitting free passage of the rib profile,
   movement of the piston in a direction from the first end toward the second end of the body to a predetermined first position being permitted with the teeth of the profile of one rib passing over the stop, and
   means within the body cooperating with the stem in said first position permitting rotation of the stem to change the positions of the ribs relative to their locations in the slots, movement of the piston from the predetermined first position toward the body first end permitted with the teeth of the profile of the other rib passing over the stop, and retraction of the piston from the body first end toward the second end prevented by the teeth of the profile of said other rib engaging the stop within the body.

2. A non-reusable syringe as in claim 1 wherein said means within the body forming the pair of slots comprises an annular member attached to the internal wall of the body, the slots formed in said annular member.

3. A syringe according to claim 2 wherein the annular member has a central circular aperture through which the stem passes and in which the two slots are provided, the stop being fixed in one of said slots.

4. A syringe according to claim 3, further comprising a second pair of ribs on the stem, the pair of ribs having the ratchet tooth profile having a greater radial extension than the second pair of ribs.

5. A syringe according to claim 4 wherein the second pair of ribs do not have a ratchet tooth profile and have a shorter radial extension, so that they may pass freely through the central aperture of the annular member.

6. A syringe according to claim 1 wherein the body of the syringe is a cylindrical barrel and further comprising an end cap which is welded to the body in fluid-tight manner.

7. A syringe according to claim 3 wherein the pair of ribs on the stem are diametrically opposed.

8. A syringe according to claim 2 wherein the means permitting rotation comprises a groove on each of said ribs below the ratchet tooth profile toward the first end of the body, said annular member disposed in said rib grooves where the stem is in said predetermined first position to permit rotation of the stem.

9. A syringe according to claim 5 wherein the means permitting rotation comprises a groove on each of said ribs below the ratchet tooth profile toward the first end of the body, said annular member disposed in said rib grooves where the stem is in said predetermined first position to permit rotation of the stem.

* * * * *